(12) United States Patent
Dixit et al.

(10) Patent No.: US 7,988,993 B2
(45) Date of Patent: Aug. 2, 2011

(54) ORAL CONTROLLED RELEASE DOSAGE FORM

(75) Inventors: Manesh Dixit, Sunrise, FL (US); Chih-Ming Chen, Taipei (TW); Xiu Xiu Cheng, Weston, FL (US); Jianbo Xie, Davie, FL (US)

(73) Assignee: Andrx Pharmaceuticals, Inc., Davie, FL (US)

( * ) Notice: Subject to any disclaimer, the term of this patent is extended or adjusted under 35 U.S.C. 154(b) by 887 days.

(21) Appl. No.: 10/726,024

(22) Filed: Dec. 2, 2003

(65) Prior Publication Data

US 2004/0156896 A1 Aug. 12, 2004

Related U.S. Application Data

(60) Provisional application No. 60/431,954, filed on Dec. 9, 2002.

(51) Int. Cl.
*A61K 9/48* (2006.01)
*A61K 9/26* (2006.01)

(52) U.S. Cl. ........................ 424/452; 424/463

(58) Field of Classification Search .................. 424/469, 424/452
See application file for complete search history.

(56) References Cited

U.S. PATENT DOCUMENTS

| | | | |
|---|---|---|---|
| 4,519,801 A | 5/1985 | Edgren |
| 4,612,008 A | 9/1986 | Wong et al. |
| 4,783,337 A | 11/1988 | Wong et al. |
| 4,874,613 A | 10/1989 | Hsiao |
| 4,894,240 A | 1/1990 | Geoghegan et al. |
| 4,952,402 A | 8/1990 | Sparks et al. |
| 5,023,088 A | 6/1991 | Wong et al. |
| 5,082,668 A | 1/1992 | Wong et al. |
| 5,654,005 A | 8/1997 | Chen et al. |
| 5,773,478 A | 6/1998 | Richards et al. |
| 5,837,284 A | 11/1998 | Mehta et al. |
| 5,874,090 A | 2/1999 | Baker et al. |
| 5,908,850 A | 6/1999 | Zeitlin et al. |
| 5,914,129 A | 6/1999 | Mauskop |
| 6,228,398 B1 | 5/2001 | Devane et al. |
| 6,312,728 B1 * | 11/2001 | Beiman et al. ............ 424/490 |
| 6,322,819 B1 | 11/2001 | Burnside et al. |
| 6,340,476 B1 | 1/2002 | Midha et al. |
| 6,344,215 B1 | 2/2002 | Bettman et al. |
| 6,355,656 B1 | 3/2002 | Zeitlin et al. |
| 6,368,626 B1 | 4/2002 | Bhatt et al. |
| 6,372,254 B1 | 4/2002 | Ting et al. |
| 6,417,184 B1 | 7/2002 | Ockert |
| 6,419,952 B2 | 7/2002 | Wong et al. |
| 6,419,960 B1 | 7/2002 | Krishnamurthy et al. |
| 6,475,493 B1 * | 11/2002 | Mulye ...................... 424/400 |
| 6,495,154 B1 | 12/2002 | Tam et al. |
| 6,500,459 B1 | 12/2002 | Chhabra et al. |
| 6,503,950 B1 | 1/2003 | Ockert |
| 6,531,489 B2 | 3/2003 | Harris et al. |
| 6,555,127 B2 | 4/2003 | Steiner |
| 6,555,136 B2 | 4/2003 | Midha |
| 6,602,521 B1 | 8/2003 | Ting et al. |
| 6,627,223 B2 | 9/2003 | Percel et al. |
| 6,635,284 B2 | 10/2003 | Mehta et al. |
| 6,638,533 B2 | 10/2003 | Krsek |
| 6,673,367 B1 | 1/2004 | Goldenheim et al. |
| 6,692,767 B2 | 2/2004 | Burnside et al. |

FOREIGN PATENT DOCUMENTS

| | | |
|---|---|---|
| EP | 0 320 097 A1 | 6/1989 |
| WO | WO 98/06380 | 2/1998 |
| WO | WO 98/14168 | 4/1998 |
| WO | WO 98/23263 | 6/1998 |
| WO | WO 99/03471 | 1/1999 |
| WO | WO 99/62496 | 12/1999 |
| WO | WO 00/35450 | 6/2000 |

* cited by examiner

*Primary Examiner* — Sreeni Padmanabhan
*Assistant Examiner* — Renee Claytor
(74) *Attorney, Agent, or Firm* — Florek & Endres PLLC (57) ABSTRACT

A dosage form that provides a controlled release solid dosage form for the oral administration of a central nervous system stimulant, preferably methylphenidate hydrochloride.

5 Claims, 6 Drawing Sheets

ORAL CONTROLLED RELEASE DOSAGE FORM

The present application claims priority to U.S. Provisional Patent No. 60/431,954, filed Dec. 9, 2002.

BACKGROUND OF THE INVENTION

1. Field of the Invention

The present invention relates to the improved dosing of medication. Specifically, this invention improves the therapeutic effect of a central nervous system stimulant such as methylphenidate hydrochloride by delivering the medication over a predetermined period of time. In the present invention an initial immediate dose of the central nervous system stimulant is delivered followed by a second controlled dose of the medication from a single oral dosage form. The invention helps improve patient compliance and decreases the need for additional daily doses of the medication.

2. Description of the Related Art

Methylphenidate is a central nervous system stimulant used to treat Attention-Deficit Disorder (ADD) and Attention-Deficit Hyperactivity Disorder (ADHD), available commercially as, e.g. RITALIN SR®, CONCERTA™, METADATE™ CD capsules and METEADATE™ ER Tablets. The beneficial results seen by clinicians in the treatment of ADD and ADHD has resulted in widespread use of methylphenidate in more than two million patients annually. Methylphenidate exists in four separate optical isomers, l-threo, d-erythro, d-threo and l-erythro, with the threo pair of enantiomers (racemate) of methylphenidate hydrochloride generally administered for the treatment of ADD and ADHD. Methylphenidate hydrochloride is a mild central nervous system stimulant with pharmacological properties similar to that of amphetamines. The side effects which are associated with the use of methylphenidate include anorexia, weight loss, insomnia, dizziness and dysphoria. Methylphenidate is categorized by the DEA as a Schedule II controlled substance because it produces a euphoric effect when administered intravenously or through inhalation or ingestion, and thus carries a high potential for abuse.

Numerous sustained release formulations of methylphenidate which provide for a slow release of the medication over a predetermined period of time have been developed and some of these formulations are described in U.S. Pat. Nos. 6,340,476, 6,344,215, 6,372,254, 6,368,626, 5,837,284 and 6,034,101, incorporated herein by reference. However, when methylphenidate is delivered at a steady state over a sustained period of time, acute tolerance often develops. The undesirable clinical effects of steady state sustained release formulations are overcome by multiple dosing whereby the intensity of the therapeutic effects of the methylphenidate can be maintained.

The sustained release tablet form of methylphenidate hydrochloride described in U.S. Pat. No. 6,034,101 and incorporated herein by reference, comprises a sustained release tablet that provides an ascending dose of the drug. This does not model the multiple dose administration of immediate release methylphenidate hydrochloride tablets. Controlled release of the medication is achieved by a hydrogel matrix.

The sustained release formulation of methylphenidate described in U.S. Pat. No. 5,837,284 and incorporated herein by reference, is made up of two groups of particles. One group provides a substantially immediate dose of methylphenidate drug, the other supplies a dose of methylphenidate delayed by about 2 to 7 hours.

Sustained release formulations of methylphenidate have been developed, which provide for the slow release of the drug over the course of the day. However it has been observed that peak plasma concentrations of the drug are lower when sustained release formulations are used. Studies have shown that sustained release formulations of methylphenidate have been shown to have lower efficacy than conventional dosage forms.

Although the prior art controlled release formulation provide steady increases in the blood level of methylphenidate hydrochloride, they may be less than desirable because their delivery rates do not mimic the plasma profile of multiple dose regimens known to prevent tolerance.

To overcome the previously mentioned problems with sustained delivery of methylphenidate, the present invention provides the needed delivery system whereby the drug can be administered in a single dose and provide the needed delivery rate so that tolerance to its effects will not develop. Furthermore, a single effective daily dose will eliminate the risk of theft or loss of the second dose and increase the medications overall therapeutic value.

SUMMARY OF THE INVENTION

The present invention is a novel unitary dosage formulation of a central nervous system stimulant which provides for an enhanced dosage delivery efficiency which effectively reproduces the effects of multiple dose therapy. The active ingredient is delivered such that plasma peaks and troughs experienced in multiple dosing are present. Thus, the invention provides a single dose delivery system that attains the desired therapeutic multiple dosing regimen plasma levels.

One embodiment of the present invention provides a unitary controlled release solid dosage form for the oral administration of a central nervous system stimulant such as methylphenidate hydrochloride. The pharmaceutical formulation contains a drug core or tablet, a controlled release coating surrounding the core or tablet, an immediate release layer applied to the controlled release coating and an optionally aesthetic overcoat covering. The core tablet is a mixture of the active pharmaceutical compound, a diluent, a binding agent and optionally other conventional processing aids such as anti-sticking agents, fillers and glidants. The controlled release coating surrounds the core tablet and is comprised of an enteric polymer and optionally other conventional processing aids such as surfactants, plasticizers and anti-sticking agents. The immediate release drug layer is applied over the controlled release coating and is a mixture of active ingredient, a binder, and an optionally a stabilizer. An overcoat or aesthetic coating may be applied to the final dosage form.

In a preferred embodiment, the present invention is a controlled release pharmaceutical dosage formulation for oral administration comprising a core with a central nervous system stimulant, an enteric polymer surrounding the core and an immediate release layer comprising a central nervous system stimulant and a stabilizer, wherein the formulation when administered to humans exhibits one of the following characteristics: (a) a maximum plasma concentration up to about 20 ng/ml, preferably, a maximum plasma concentration of about 3 to about 20 ng/ml; (b) an $AUC_{0-24}$ up to about 200 ng/ml, preferably, an $AUC_{0-24}$ of about 30 to about 200 (ng hr)/ml; (c) a $T_{max}$ of about 3 to about 12 hours; or any combination of the foregoing.

In a preferred embodiment, the present invention is a controlled release pharmaceutical dosage formulation for oral administration comprising a core with a central nervous system stimulant, an enteric polymer surrounding the core and an immediate release layer comprising a central nervous system stimulant and a stabilizer. Wherein, the active ingredient when administered to humans is characterized by a plasma peak for the immediate release layer ($T_{max1}$) between 1 and 5 hours, a plasma peak for the controlled release core ($T_{max2}$) between 4 and 12 hours, and a plasma trough ($T_{min}$) between 2 and 7 hours in between the two peak plasma levels.

Other objects, features and advantages of the invention are not taught in the prior art but will be more apparent to those versed in the art from the following specifications, taken in conjunction with the accompanying claims.

DETAILED DESCRIPTION OF THE INVENTION

The invention provides a controlled release formulation of a central nervous system stimulant, preferably methylphenidate and its pharmaceutically acceptable salts, for oral administration, said formulation comprising:
(1) a core comprising:
  (a) central nervous system stimulant such as methylphenidate and its pharmaceutically acceptable salts, isomers or pharmaceutically acceptable mixture thereof;
  (b) a binding agent;
  (c) a diluent; and
(2) a controlled release coating surrounding the core comprising;
  (a) an enteric polymer;
  (b) a plasticizer; and
  (c) optionally a anti-sticking agent; and
(3) an immediate release drug layer comprising;
  (a) a central nervous system stimulant, preferably methylphenidate and its pharmaceutically acceptable salts, isomers or pharmaceutically acceptable mixture thereof;
  (b) a binder; and
  (c) optionally a stabilizer; and
(4) optionally an overcoat comprising;
  (a) a coating agent.

The core of the present invention comprises about 1-50% based on the total weight of the core of a central nervous system stimulant and preferably 5-40% and most preferably 10-25% of the total weight of the core.

The core should also comprise a binding agent. The binding agent can be any type of material commonly known in the pharmaceutical art. Acceptable binder materials can be polymeric, non-polymer, water soluble or water insoluble. Preferably, the binding agent employed in the core is water soluble, gels or swells (hydrogel forming polymer) in the presence of water. Some of the commonly known binders are acacia, alginic acid, sodium carboxymethylcellulose, microcrystalline cellulose, dextrin, ethylcellulose, gelatin, liquid glucose, polyvinyl pyrrolidone, carboxyvinyl polymer, methylcellulose, hydroxymethyl cellulose, low molecular weight polyethylene oxide polymers, hydroxyethyl cellulose, hydroxypropyl cellulose, hydroxypropyl methylcellulose (HPMC), gums, acrylate polymers, methacrylate polymers, maltodextrin and mixtures of the foregoing. The preferred binder for use in the core is hydroxypropylmethyl cellulose, such as the material sold as Methocele™ K-100M. The amount of binder in the core should comprise 1 to about 50% of the total weight of the core and preferably about 3 to about 40% of the total weight of the core.

The core may optionally contain a diluent or filler. If a diluent or filler is employed in the core, it can be any type of diluent commonly known in the art such as sugars, starches or vegetable oils. Examples of some preferred diluent are lactose monohydrate, calcium carbonate, calcium sulfate, microcrystalline cellulose, calcium phosphate, dextrin, dextrose, maltitol, maltose, starch, sucrose or talc. In a preferred embodiment of the present invention, the diluent used in the core of the tablet is lactose monohydrate. If a diluent is used in the core, the amount should be about 1% to about 95% based on the total weight of the core, preferably 25% to 90% based on the total weight of the core, and most preferably about 40% to about 85% based on the total weight of the core.

The core may also optionally contain a lubricant agent. Lubricant agents are used to facilitate manufacturing of the formulation, some examples of suitable anti-sticking agents include, talc, glyceryl monostearates, calcium stearate, magnesium stearate, stearic acid, glyceryl behenate, and polyethylene glycol, and are preferably present at no more than approximately about 0.05 to about 15% based upon the total weight of the core, preferably about 0.1 to about 10% based upon the total weight of the core and most preferably about 0.5 to about 5% based upon the total weight of the core.

The core of the present invention is preferably formed by mixing the core ingredients and tableting the mixture using techniques commonly known in the art. The core may also be formed by granulating the core ingredients and compressing the granules with or without the addition of an anti-sticking agent into a tablet.

In a preferred embodiment the core is subsequently coated with a controlled release coating. This controlled release coating is applied by conventional coating techniques, such as pan coating or fluid bed coating using solution, suspension or dispersion of polymeric material in water or suitable organic solvents. A particularly preferred controlled release coating employs an enteric polymer. The controlled release coating comprises about 2 to about 50 weight percent of the coated core, preferably about 5 to about 30 weight percent of the coated core. Preferably, the enteric polymer employed in the controlled release coating is selected from the group consisting of zein, methacrylic acid copolymers, cellulose acetate phthalate, hydroxypropyl methylcellulose phthalate, hydroxypropyl methylcellulose acetate succinate, cellulose acetate trimellitate, shellac, polyvinyl acetate phthalate or mixtures thereof. The amount of enteric polymer material in the controlled release coating is preferably about 5 to about 95 weight percent, preferably about 10 to about 70 weight percent based on the total weight of the controlled release coating. In one embodiment of the invention the amount of enteric polymer material in the controlled release coating is 45 to 80 weight percent based on the total weight of the controlled release coating. In a preferred embodiment of the present invention, a mixture of zein and methacrylic acid copolymer is employed. The methacrylic acid copolymer is selected from the group of enteric polymers, preferably Eudragit S. The preferred ratio of zein to methacrylic acid copolymer is 1:5 to 5:1 with the most preferred ratio being 2:1 to 4:1.

The controlled release coating also preferably contains plasticizers. Plasticizers which may be used include any of those known to those skilled in the art, including but not limited to, acetyltributyl citrate, triacetin, acetylated monoglyceride, rape oil, olive oil, sesame oil, coconut oil, poloxamer, acetyltriethyl citrate, glycerin, sorbitol, diethyloxalate, diethylmalate, diethylfumerate, dibutylsuccinate, diethylmalonate, dioctylphthalate, dibutylphthalate, dibutylsebacate, triethyl citrate, tributylcitrate, glyceroltributyrate, polyethylene glycol, propylene glycol and mixtures thereof. The preferred plasticizer is acetyltributyl citrate. The amount of plasticizer employed in the controlled release coating can range from about 0.1 to about 30%, preferably about 0.5 to about 15% and most preferably about 1 to about 5% based on the total weight of the controlled release coating.

The controlled release coating may also include an anti-sticking agent such as those selected from the group consisting of talc, colloidal silica dioxide, magnesium stearate, magnesium silicate, glyceryl monostearates, calcium stearate or steric acid. The preferred anti-sticking agent is talc. If an anti-sticking agent is employed in the controlled release coating, the amount employed should range from about 10 to about 70 percent, and most preferably 20-60% based on the total weight of the coating.

In a preferred embodiment of the present invention, a second coating is applied to the controlled release coating to form an immediate release portion of the dosage formulation. This second or immediate release layer is comprised of the pharmaceutically central nervous system stimulant and a binder that preferably is a pharmaceutically acceptable water-soluble or rapidly dispersing material. The binder employed can be any type of binding agent commonly known in the art such as those described above. In a preferred embodiment of the present invention, the binder for the immediate release coating is a water soluble polymer such as hydroxypropyl methylcellulose, commercially available under the trade name Methocel® E-5. A preferred composition, the binder should comprise about 40 to about 70% of the total weight of the immediate release layer and preferably about 45 to about 60 weight percent of the total weight of the immediate release layer.

The immediate release coating may also contain a stabilizer for the pharmaceutically active compound. In a preferred embodiment of the present invention, a stabilizer is a material that causes the pH of the immediate release coating solution to have a pH of about 7 or below. The preferred stabilizer is selected from the group consisting of organic acids, inorganic acids, acid addition salts, buffers and combinations thereof. The most preferred stabilizers are organic acids such as fumaric acid. The preferred concentration of the stabilizer is about 0.001 to about 10%, preferably about 0.005 to about 5% and most preferably about 0.01 to about 2% based upon the total weight of the immediate release coating.

Finally, the immediate release coating may be coated with an overcoat, polishing coat or color coat using any of the methods commonly known in the industry.

The dissolution profile of the dosage form prepared according to the present invention is pH dependent and should exhibit the following dissolution profile when tested in a USP type 2 (paddle) apparatus at 50 rpms in 900 ml of phosphate buffer with a of pH 7.5 and at 37° C.

| | DRUG RELEASED | |
|---|---|---|
| Time (hours) | Preferred | Most Preferred |
| 1 | 1-35% | 5-30% |
| 2 | 5-40% | 10-35% |
| 4 | * NLT 25% | NLT 30% |
| 10 | NLT 70% | NLT 80% |

* NLT = Not Less Than

In the preparation of the tablets of the invention, various conventional well known solvents may be used to prepare the granules and apply the external coating to the tablets of the invention. In addition, various diluents, excipients, anti-sticking agents dyes, pigments, dispersants etc. which are disclosed in Remington's Pharmaceutical Sciences $20^{th}$ Edition, 2000, and the Handbook of Pharmaceutical Excipients, Third Edition, by Arthur H. Kibbe, which are incorporated herein by reference, may be used to optimize the formulations of the invention.

DESCRIPTION OF THE PREFERRED EMBODIMENTS

Example 1

A batch of once a day controlled release methylphenidate tablets in accordance with the present invention is prepared by first forming methylphenidate cores containing approximately 22 mg of methylphenidate HCl, and 14 mg methylphenidate HCl in the immediate release layer as follows:
(a) Core 73.35 g of methylphenidate HCl and 396.65 g of lactose monohydrate, NF, 25.0 g of hydroxypropyl methylcellulose (Methocel K-100M Premium), 2.5 g of colloidal silicon dioxide (CAB-O-SIL) are delumped by passing the compounds through a 20 mesh screen and then mixed with in a suitable blender for 20 minutes. 2.5 g of magnesium stearate is screened and added to the drug mixture and blended for an additional 5 minutes. After all the ingredients are blended together, the mixture is compressed into tablets using a rotary press fitted with 9/32" round standard concave punches. The target hardness is about 5 kp.

The core tablets are then coated with a controlled release coating as follows:
(b) Controlled Release Coating 8.40 g of methacrylic acid copolymer (Eudragit S 100), 25.24 g of zein NF (regular Grade F4000), 2.81 g acetyltributyl citrate NF, and 33.68 g of talc USP are dispersed in 312.53 g of isopropyl alcohol USP and 56.77 g of purified water (USP) while stirring with a homogenizer. An additional 28.10 g of isopropyl alcohol is used to rinse the homogenizer and other equipment. The rinse isopropyl alcohol is added to the coating suspension. The coating suspension is then sprayed onto the tablets in a fluidized bed coater employing the following conditions: exhaust temperature of 25-35° C.; atomization pressure of approximately 1 bar; and a spray rate of 2-6 ml/min.

Once the controlled release coating suspension has been applied to the core tablets, the controlled release coated tablets are transferred from the fluidized bed coater onto drying trays and placed in an oven at 55-65° C. for approximately 16 hours to allow curing of the coating. Once the controlled release coated tablets are cured, an immediate release methylphenidate HCl coating is applied to the controlled release coated tablets as follows:

(c) Immediate Release Coat 19.202 g of methylphenidate hydrochloride, 19.202 g of hydroxypropyl methylcellulose (Methocel® E5 Premium) and is dissolved in 245.636 g of purified water USP. The mixture is rinsed with 100 g of purified water USP and then 8.951 g of Opadry® White YS-1-7003 is dispersed into 80.559 g of water and mixed for 1 hour. The drug solution is sprayed onto the controlled release tablets using a fluidized bed coater employing the following conditions: exhaust temperature of 40-50° C.; atomization pressure of approximately 1 bar; and a spray rate of 2-5 ml/min.

Once the immediate release coating solution has been consumed, the Opadry® dispersion is sprayed on the tablets. The immediate release coated tablets are dried in the fluidized bed coater for approximately 20 minutes. The final tablets have approximately 14 mg of methylphenidate HCl in the immediate release coating and approximately 22 mg of methylphenidate HCl in the core.

The resulting tablets were tested in human subjects along with CONCERTA™ brand methylphenidate HCl tablets. In a randomly assigned test the subjects were given either a single dose of 36 mg of methylphenidate controlled release formulation described herein or an equivalent amount in a single dose of CONCERTA™ brand sustained release methylphenidate HCl tablet. The results of the in vivo testing are provided in TABLE 1 as depicted by the graph in FIG. 1.

TABLE 1

Figure 1:
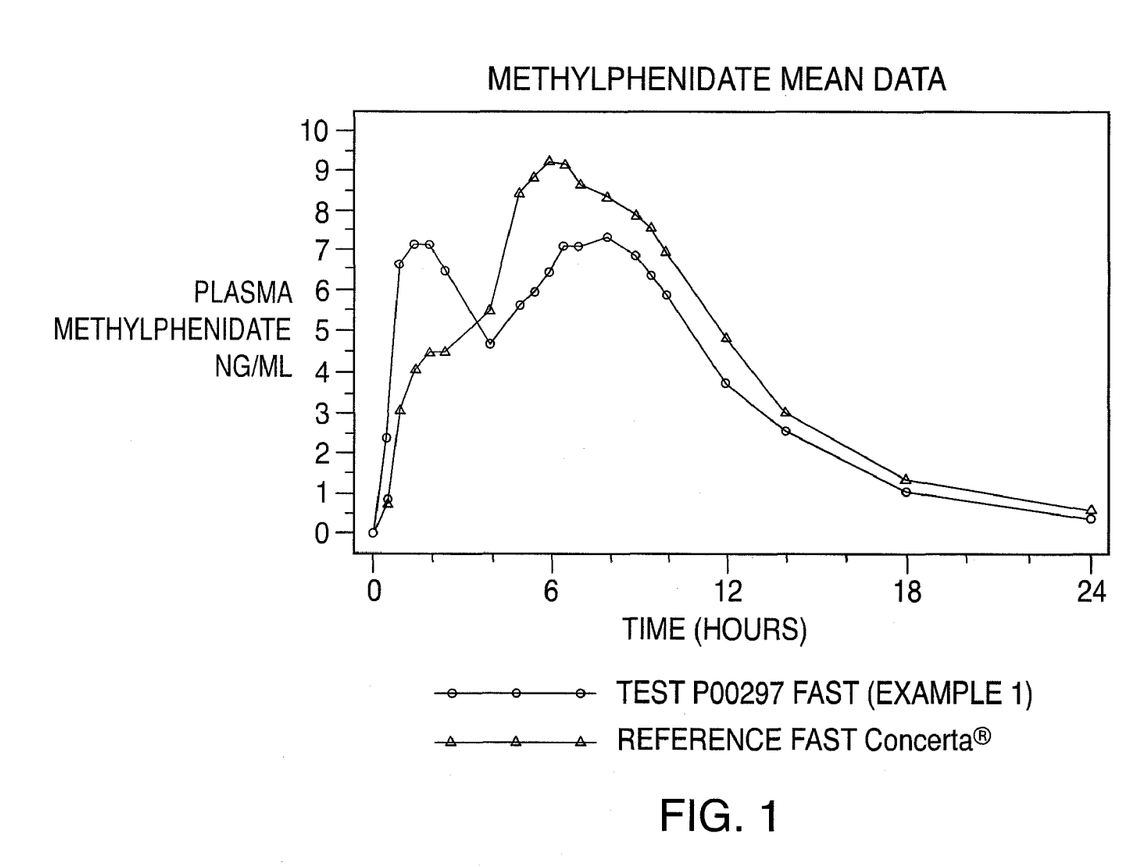
FIG. 1 is a graph depicting mean plasma concentration, under fasting conditions, of a single controlled release dose of methylphenidate hydrochloride from the formulation as described in Example 1 in ng/ml over a 24 hour period of the verses the mean Plasma concentration of an equivalent dose of the commercially available controlled release form of methylphenidate (CONCERTA™).

| | Mean Plasma concentration | |
|---|---|---|
| | Methylphenidate controlled release | CONCERTA ™ |
| 2 hr | 7.1 ng/ml | 4.5 ng/ml |
| 4 hr | 4.7 ng/ml | 5.5 ng/ml |
| 6 hr | 6.4 ng/ml | 9.3 ng/ml |
| 8 hr | 7.4 ng/ml | 8.4 ng/ml |
| 12 hr | 3.8 ng/ml | 4.9 ng/ml |
| 18 hr | 1.1 ng/ml | 1.4 ng/ml |

Figure 2:
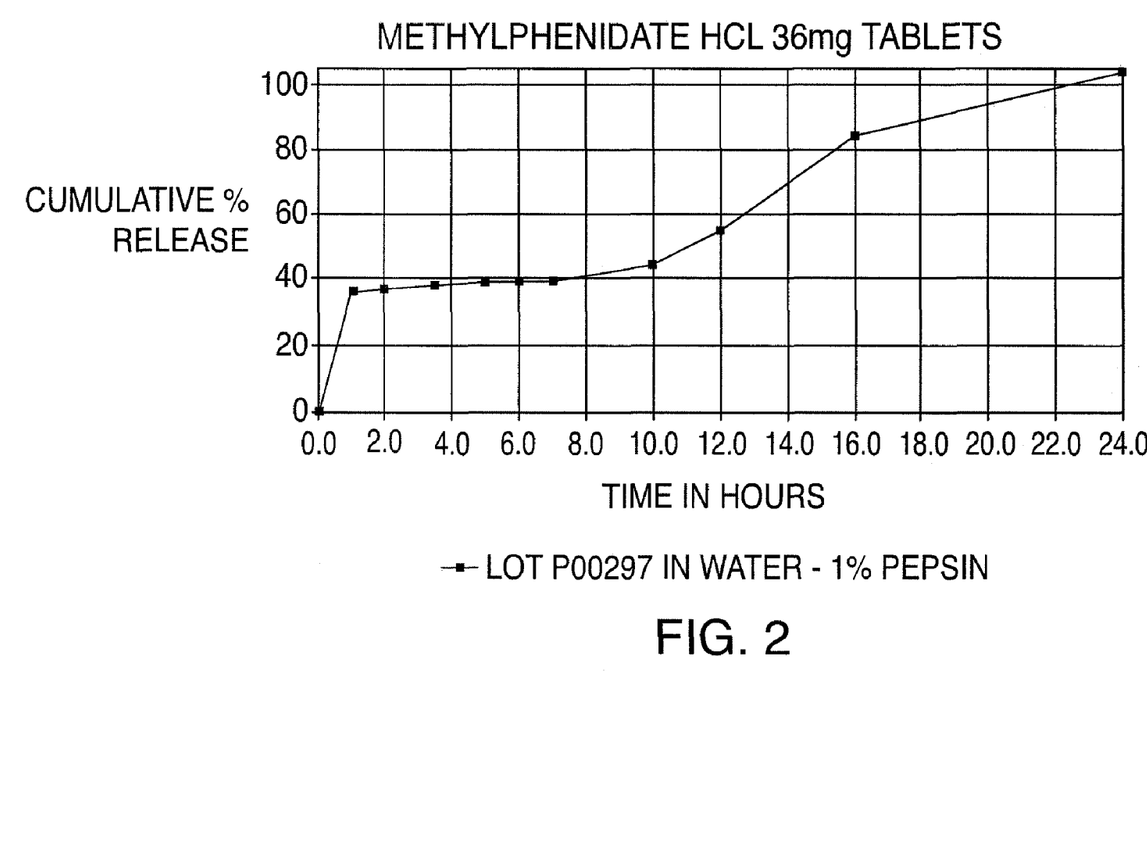
FIG. 2 is a graph depicting the dissolution profile over a 24 hour period in water-1% pepsin for the formulation as described in Example 1.

Dissolutions studies for drug release from the formulation of Example 1 were conducted with USP apparatus No 1, at 100 rpm in 500 ml of Water-1% Pepsin at intervals over 24 hours are as follows in TABLE 2 as depicted in graph in FIG. 2.

TABLE 2

| | % dissolved |
|---|---|
| 1 hour | 37% |
| 2 hours | 37% |
| 3.5 hours | 38% |
| 5 hours | 39% |
| 7 hours | 40% |
| 12 hours | 55% |
| 24 hours | 104% |

Example 2

A batch of once a day controlled release methylphenidate tablets in accordance with the present invention is prepared by first forming methylphenidate cores containing approximately 28 mg of methylphenidate HCl, and 8 mg methylphenidate HCl in the immediate release layer as follows:

(a) Core 93.35 g of methylphenidate HCl, 351.65 g of lactose monohydrate, NF, 50.0 g of hydroxypropyl methylcellulose (Methocel K-100M Premium) and 2.5 g of colloidal silicon dioxide (CAB-O-SIL) are delumped by passing the compounds through a 20 mesh screen and then mixed in a suitable blender for 20 minutes. 2.5 g of magnesium stearate is screened and added to the drug mixture and blended for an additional 5 minutes. After all the ingredients are blended together, the mixture is compressed into tablets using a rotary press fitted with 9/32" round standard concave punches. The target hardness is about 5 kp.

The core tablets are then coated with a controlled release coating as follows:

(b) Controlled Release Coating 8.40 g of methacrylic acid copolymer (Eudragit S 100), 25.24 g of zein NF (regular Grade F4000), 2.81 g acetyltributyl citrate, NF and 33.68 g of talc USP are dispersed in 312.53 g of isopropyl alcohol USP and 56.77 g of purified water (USP) while stirring with a homogenizer. An additional 28.10 g of isopropyl alcohol is used to rinse the homogenizer and other equipment. The rinse isopropyl alcohol is added to the coating suspension. The coating suspension is then sprayed onto the tablets in a fluidized bed coater employing the following conditions: exhaust temperature of 25-35° C.; atomization pressure of approximately 1 bar; and a spray rate of 2-6 m/min.

Once the controlled release coating suspension has been applied to a lot of core tablets, the controlled release coated tablets are transferred from the fluidized bed coater onto drying trays and placed in an oven at 55-65° C. for approximately 16 hours to allow curing of the coating. Once the controlled release coated tablets are cured an immediate release methylphenidate HCl coating is applied to the controlled release coated tablets as follows:

(c) Immediate Release Coat 10.889 g of methylphenidate hydrochloride, 10.889 g of hydroxypropyl methylcellulose (Methocel® E5 Premium) and is dissolved in 220.261 g of purified water USP. The mixture is rinsed with 50 g of purified water USP and then 8.251 g of Opadry® White YS-1-7003 is dispersed into 74.259 g of water and mixed for 1 hour. The drug solution is sprayed onto the controlled release tablets using a fluidized bed coater employing the following conditions: exhaust temperature of 40-50° C.; atomization pressure of approximately 1 bar; and a spray rate of 2-5 ml/min.

Once the immediate release coating solution has been consumed, the Opadry® dispersion is sprayed on the tablets. The immediate release coated tablets are dried in the fluidized bed coater for approximately 20 minutes. The final tablets have approximately 8 mg of methylphenidate HCl in the immediate release coating and approximately 28 mg of methylphenidate HCl in the core.

The resulting tablets were tested in human subjects along with CONCERTA™ brand methylphenidate HCl tablets. In a randomly assigned test the subjects were given either a single dose of 36 mg of methylphenidate controlled release formulation described herein or an equivalent amount in a single dose of CONCERTA™ brand sustained release methylphenidate HCl tablet. The results of the in vivo testing are provided in TABLE 3 as depicted by the graph in FIG. 3.

TABLE 3

Mean Plasma concentration

Figure 3:
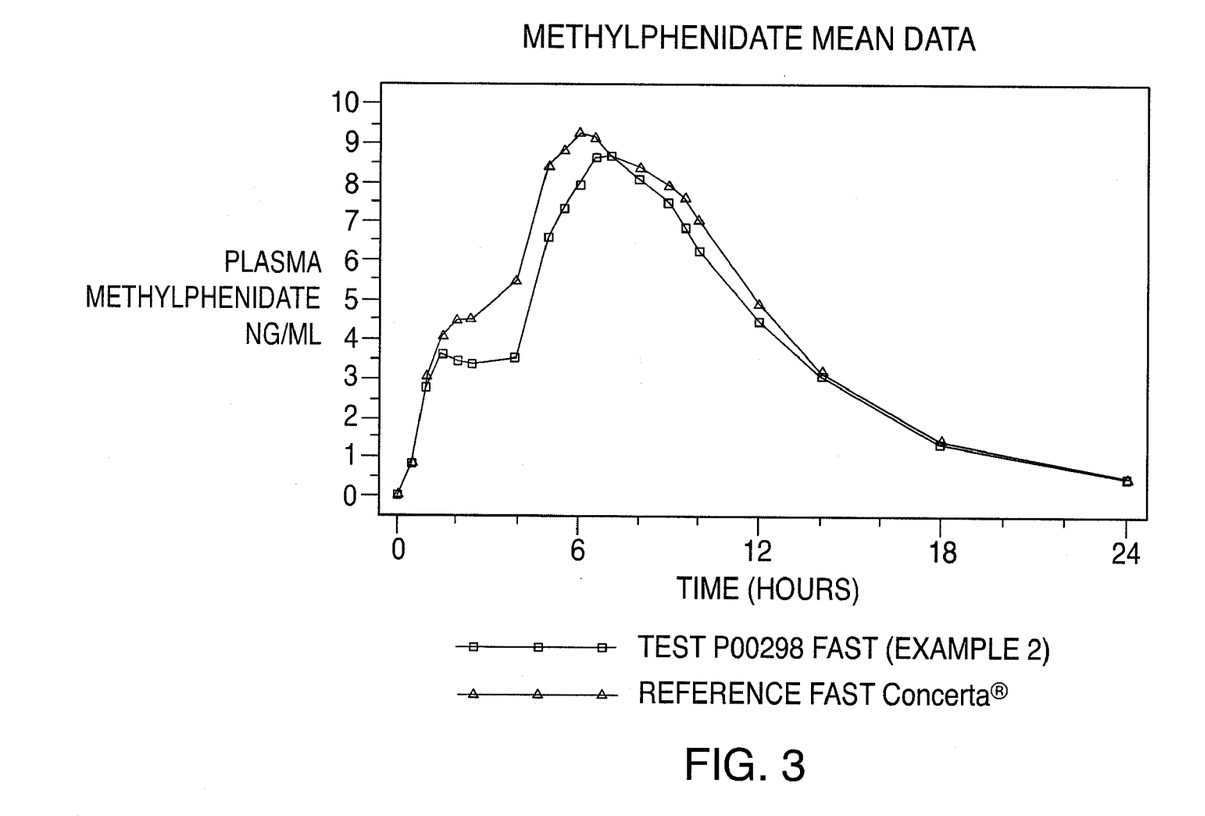
FIG. 3 is a graph depicting mean plasma concentration, under fasting conditions, of a single controlled release dose of methylphenidate hydrochloride from the formulation as described in Example 2 in ng/ml over a 24 hour period of the verses the mean Plasma concentration of an equivalent dose of the commercially available controlled release form of methylphenidate (CONCERTA™).

|  | Methylphenidate controlled release | Concerta ™ |
|---|---|---|
| 2 hr | 3.5 ng/ml | 4.5 ng/ml |
| 4 hr | 3.3 ng/ml | 5.5 ng/ml |
| 6 hr | 7.7 ng/ml | 9.3 ng/ml |
| 8 hr | 7.9 ng/ml | 8.4 ng/ml |
| 12 hr | 4.2 ng/ml | 4.9 ng/ml |
| 18 hr | 1.4 ng/ml | 1.4 ng/ml |

Example 3

Once a day controlled release methylphenidate tablets in accordance with the present invention are prepared by first forming methylphenidate cores containing approximately 27 mg of methylphenidate HCl, and 9 mg of methylphenidate HCl in the immediate release layer as follows:

(a) Core 3.708 kg of methylphenidate HCl and 15.656 kg of lactose monohydrate, NF, 1.030 kg of hydroxypropyl methylcellulose (Methocel K-100M Premium), 0.103 kg of colloidal silicon dioxide (CAB-O-SIL) are delumped by passing the compounds through a 20 mesh screen and then mixed in an appropriate blender, then screened and blended again. 0.103 kg of magnesium stearate is screened and added to the drug mixture and blended for an additional 5 minutes. After all the ingredients are blended together, the mixture is compressed into tablets using a rotary press fitted with $^{17}\!/_{64}$" round standard concave punches. The target hardness is about 6 kp.

The core tablets are then coated with a controlled release coating as follows:

(b) Controlled Release Coating 0.242 kg of methacrylic acid copolymer (Eudragit S 100), 0.725 kg of zein NF (regular Grade F4000), 0.081 kg acetyltributyl citrate, NF and 0.967 kg of talc USP are dispersed in 9.000 kg of isopropyl alcohol USP and 1.631 kg of purified water (USP) while stirring with a homogenizer. An additional 0.787 kg of isopropyl alcohol is used to rinse the homogenizer and other equipment. The rinse isopropyl alcohol is added to the coating suspension. The coating suspension is then sprayed onto the tablets in a pan coater employing the following conditions: product temperature of 30° C.; atomization pressure of approximately 20 psi; and a spray rate of approximately 30 ml/min. Remove 0.225 kg of coated tablets after spraying 11.18 kg of dispersion corresponding to a 15% weight gain of coated tablets (Batch 1).

Once the controlled release coating suspension has been applied to a lot of core tablets to give approximately 17.5% weight gain of coated tablets (Batch 2). The controlled release coated tablets are transferred from the fluidized bed coater onto drying trays and placed in an oven at 55-65° C. for approximately 16 hours to allow for curing of the coating.

Once the controlled release coated tablets are cured an immediate release methylphenidate HCl coating is applied to the controlled release coated tablets in two batches as follows:

(c) Immediate Release Coat (i) Batch 1

In the first batch, 10.931 g of methylphenidate hydrochloride, 10.931 g of hydroxypropyl methylcellulose (Methocel® E5 Premium) is dissolved in 211.760 g of purified water USP. The mixture is rinsed with 46.76 g of purified water USP. 6.862 g of Opadry® White YS-1-7003 is dispersed into 61.760 g of water and mixed for 1 hour. The drug solution is sprayed onto a 200 g batch of controlled release tablets having 15% coating level (Batch 1), using a fluidized bed coater employing the following conditions: product temperature of 45±5° C.; atomization pressure of 1±0.5 bar; and a spray rate of 2-5 ml/min.

Once the immediate release coating solution has been consumed, the Opadry® dispersion is sprayed on the tablets. The immediate release coated tablets are dried in the fluidized bed coater for approximately 20 minutes. The final tablets have approximately 9 mg of methylphenidate HCl in the immediate release coating and approximately 27 mg of methylphenidate HCl in the core.

(ii) Batch 2

In the second batch, 10.624 g of methylphenidate hydrochloride, 10.624 g of hydroxypropyl methylcellulose (Methocel® E5 Premium) is dissolved in 211.760 g of purified water USP. The mixture is rinsed with 41.232 g of purified water USP. 6.843 g of Opadry® White YS-1-7003 is dispersed into 61.760 g of water and mixed for 1 hour. The solution is sprayed onto a 200 g batch of controlled release tablets having 17.5% coating level (Batch 2), using a fluidized bed coater employing the following conditions: product temperature of 45±5° C.; atomization pressure of 1±0.5 bar; and a spray rate of 2-50 ml/min.

Once the immediate release coating solution has been consumed, the Opadry® dispersion is sprayed on the tablets. The immediate release coated tablets are dried in the fluidized bed coater for approximately 20 minutes. The final tablets have approximately 9 mg of methylphenidate HCl in the immediate release coating and approximately 27 mg of methylphenidate HCl in the core.

Figure 4:
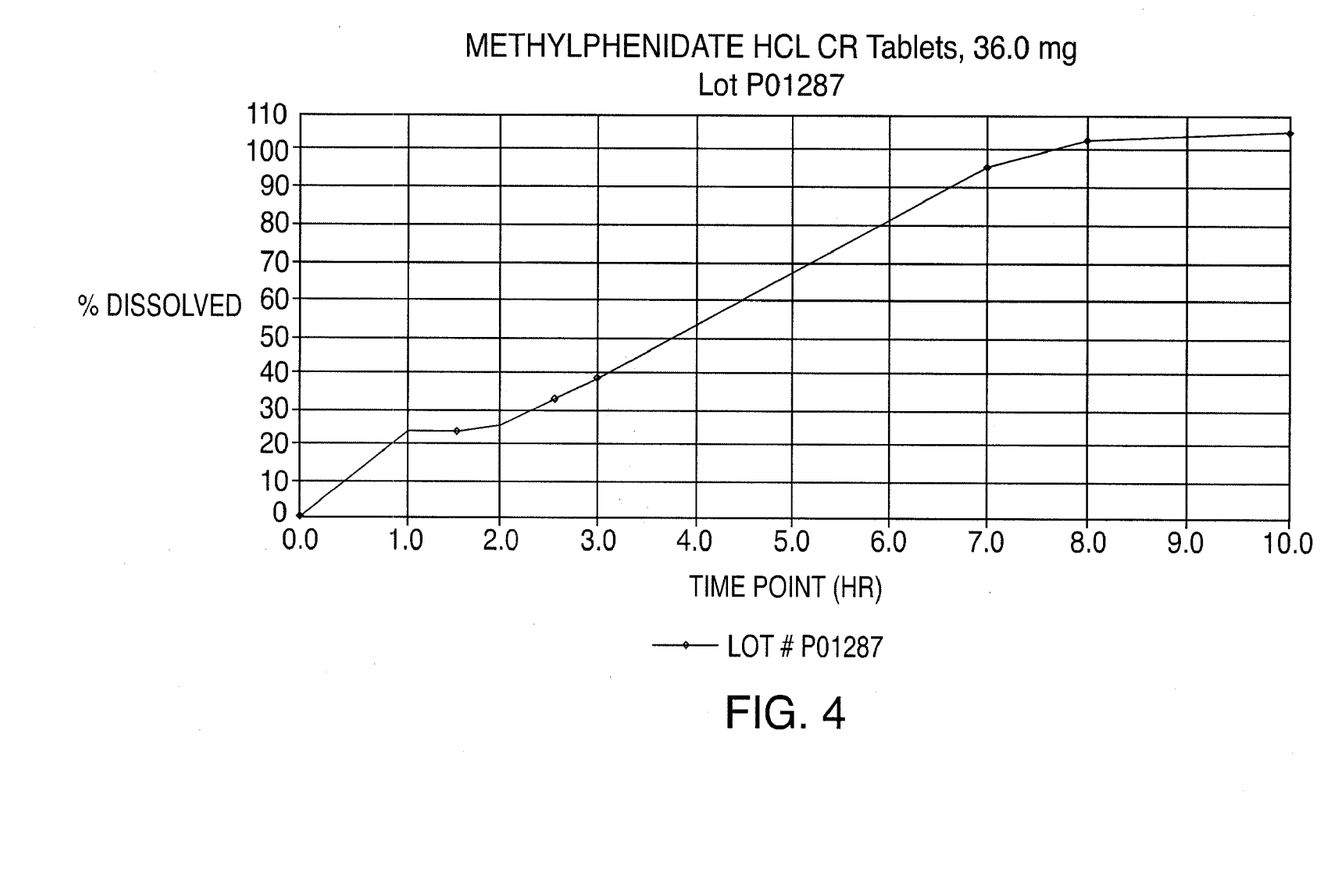
FIG. 4 is a graph depicting the dissolution profile of a preferred embodiment of the present invention. The graph shows the dissolution for 36 mg methylphenidate HCl controlled release tablets as described in Batch 1 of Example 3 over a 10 hour period.
Figure 5:
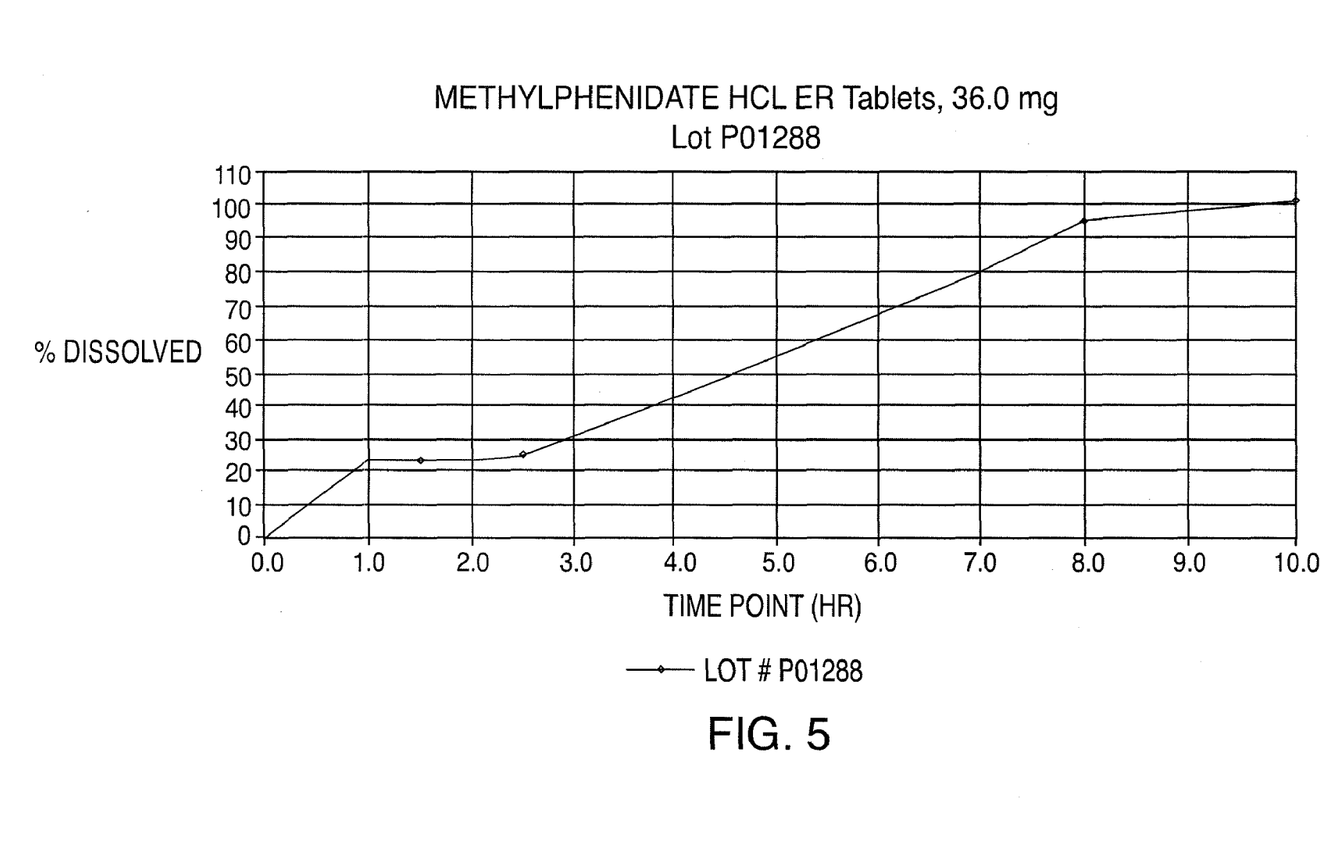
FIG. 5 is a graph depicting the dissolution profiles of a preferred embodiment of the present invention. The graph shows the dissolution for 36 mg methylphenidate HCl controlled release tablets as described in Batch 2 of Example 3 over a 10 hour period.

Dissolutions studies for drug release were conducted with USP apparatus No 1, at 100 rpm in 500 ml of pH 7.5 phosphate buffer (n=12) at intervals over 10 hour for the first and second batches as depicted in TABLE 4 and FIGS. 4 and 5, respectively, are as follows:

TABLE 4

|  | First Batch % dissolved | Second Batch % dissolved |
|---|---|---|
| 1 hour | 24% | 23% |
| 2 hours | 26% | 23% |
| 3 hours | 39% | 30% |
| 4 hours | 53% | 42% |
| 6 hours | 81% | 67% |
| 7 hours | 95% | 80% |
| 8 hours | 102% | 95% |
| 10 hours | 104% | 101% |

Example 4

A 50.22 kg batch of once a day controlled release methylphenidate tablets in accordance with the present invention is prepared by first forming methylphenidate cores containing approximately 40.5 mg of methylphenidate HCl, and 13.5 mg of methylphenidate HCl in the immediate release layer as follows:

(a) Core 5.468 kg of methylphenidate HCl and 31.6 kg of lactose monohydrate, NF, 3.038 kg of hydroxypropyl methylcellulose (Methocel K-100M Premium), 0.2025 kg of colloidal silicon dioxide (CAB-O-SIL) are delumped by passing the compounds through a 20 mesh screen and then mixed in a suitable blender for 20 minutes. 0.2025 kg of magnesium stearate is screened and added to the drug mixture and blended for an additional 5 minutes. After all the ingredients are blended together, the mixture is compressed into tablets using a rotary press fitted with 11/32" round standard concave punches. The target hardness is about 13 kp.

The tablets are then coated with a controlled release coating as follows:

(b) Controlled Release Coating 0.6271 kg of methacrylic acid copolymer (Eudragit S 100), 1.881 kg of zein NF (regular Grade F4000), 0.2090 kg acetyltributyl citrate, NF and 2.508 kg of talc USP are dispersed in 23.72 kg of isopropyl alcohol USP and 4.230 kg of purified water (USP) while stirring with a homogenizer 1.664 kg of isopropyl alcohol, USP was used to rinse the homogenizer and added to the dispersion. The coating suspension is then sprayed onto the tablets in a pan coater employing the following conditions: product temperature of 25-35° C.; atomization pressure of approximately 25-55 psi; and a spray rate of 40-100 m/min.

Once the controlled release coating suspension has been applied to the lot of core tablets, the controlled release coated tablets are dried on drying trays in an oven at 60±5° C. for 16 hours to allow for curing of the coating. Once the controlled release coated tablets are cured an immediate release methylphenidate HCl coating is applied to the controlled release coated tablets as follows:

(c) Immediate Release Coat 1.830 kg of methylphenidate hydrochloride, 1.826 kg of hydroxypropyl methylcellulose (Methocel® E5 Premium) and 0.0041 kg of fumaric acid NF are dissolved in 42.088 kg of purified water USP. 1.895 kg of Opadry® II Red 85F15266 is dispersed into 10.171 kg of water and mixed for 1 hour. The drug solution is sprayed onto the controlled release tablets using a pan coater employing the following conditions: product temperature of 35-55° C.; atomization pressure of approximately 25-55 psi; and a spray rate of 50-150 ml/min. The tablets were further film and polish coated then weighed. The final tablets have approximately 13.5 mg of methylphenidate HCl in the immediate release coating and approximately 40.5 mg of methylphenidate HCl in the core.

Figure 6:
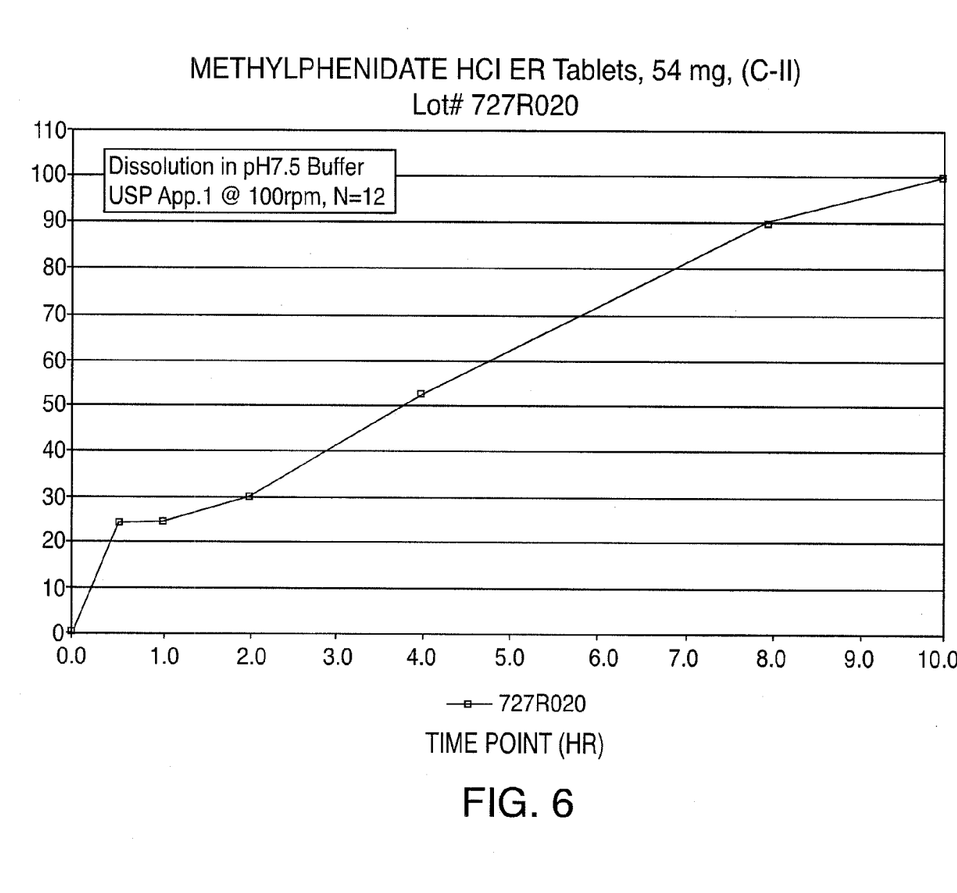
FIG. 6 is a graph depicting the dissolution profile in a pH 7.5 phosphate buffer solution of the formulation as described in Example 4.

The dissolution profile for the formulations in Example 4 was conducted with USP apparatus No 1, at 100 rpm, N=12 and pH 7.5 phosphate buffer at intervals over 10 hours, depicted in the graph of FIG. 6 and TABLE 5 as follows:

TABLE 5

| Time | % dissolved |
|---|---|
| 0.5 hour | 24% |
| 1 hour | 24% |
| 2 hours | 30% |
| 4 hours | 53% |
| 8 hours | 90% |
| 10 hours | 100% |

The resulting tablets for the formulations in Example 4 were tested in human subjects along with CONCERTA™ brand methylphenidate HCl tablets. Subjects were given either a single dose of 54 mg of methylphenidate controlled release formulation described herein or an equivalent amount in a single dose of CONCERTA™ brand sustained release methylphenidate HCl tablet under fasting and non-fasting conditions. The results of the in vivo testing are provided in TABLE 6 and TABLE 7 representing fasting and non-fasting conditions, respectively.

TABLE 6

(FASTING)
N = 28

| | Methylphenidate controlled release | Concerta ™ | % Ratio | Lower Upper Limit, Limit |
|---|---|---|---|---|
| $C_{max}$ | 14.92 | 15.49 | 96.30 | 90.79, 102.15 |
| $AUC_{inf}$ | 142.16 | 143.58 | 99.01 | 95.73, 102.17 |
| $T_{max2}$ | 7.10 | 6.01 | 118.13 | |

TABLE 7

(NON-FASTING)
N = 23

| | Methylphenidate controlled release | Concerta ™ | % Ratio | Lower Upper Limit, Limit |
|---|---|---|---|---|
| $C_{max}$ | 13.69 | 14.37 | 95.30 | 88.83, 102.24 |
| $AUC_{inf}$ | 145.32 | 153.22 | 94.84 | 91.95, 97.83 |
| $T_{max2}$ | 9.01 | 6.32 | 142.57 | |

While certain preferred and alternative embodiments of the invention have been set forth for purposes of disclosing the invention, modifications to the disclosed embodiments may occur to those who are skilled in the art. Accordingly, this specification is intended to cover all embodiments of the invention and modifications thereof which do not depart from the spirit and scope of the invention.

We claim:

1. A controlled release methylphenidate tablet consisting of:
   (A) an immediate release methylphenidate coating consisting of;
      (a) 30-60 weight percent based upon the total weight of the immediate release coating of methylphenidate or a pharmaceutically acceptable salt or isomer thereof;
      (b) 40-70 weight percent based upon the total weight of the immediate release coating of a binder; and
      (c) 0.005-5 weight percent based upon the total weight of the immediate release coating of a stabilizer;
   (B) a controlled release methylphenidate core tablet consisting of:
      (a) a compressed mixture consisting of:
         (i) 5-40 weight percent based upon the total weight of the compressed mixture of methylphenidate or a pharmaceutically acceptable salt or isomer thereof;
         (ii) 3-40 weight percent based upon the total weight of the compressed mixture of a hydrogel polymer;
         (iii) 25-90 weight percent based upon the total weight of the compressed mixture of a diluent; and
         (iv) optionally a lubricant; and
      (b) an enteric coating surrounding the core tablet consisting essentially of;
         (i) 45-80 weight percent based upon the total weight of the enteric coating of a combination of enteric polymers consisting of zein and at least one additional enteric polymer selected from the group consisting of methacrylic acid copolymers, cellulose acetate phthalate, hydroxypropyl methylcellulose phthalate, hydroxypropyl methylcellulose acetate succinate, cellulose acetate trimellitate, shellac, polyvinyl acetate phthalate or mixtures thereof;
  (ii) 0.5-15 weight percent based upon the total weight of the enteric coating of a plasticizer;
  (iii) an anti-sticking agent; and
  (iv) a surfactant; and
(C) optionally an aesthetic coating;
wherein the controlled release methylphenidate tablet exhibits the following dissolution profile when tested in a United States Pharmacopeia type 2 (paddle) apparatus at 50 rpms in 900 ml of phosphate buffer with a pH of 7.5 and at 37° C.:
  1-35% of the methylphenidate is released after 1 hour;
  5-40% of the methylphenidate is released after 2 hours; and
  not less than 70% is release after 10 hours; and
when administered to humans exhibits a plasma peak for the immediate release layer ($T_{max1}$) between 1 and 5 hours, a plasma peak for the controlled release core ($T_{max2}$) between 4 and 12 hours, and a plasma trough ($T_{min}$) between 2 and 7 hours in between the two peak plasma levels;
and wherein the immediate release methylphenidate coating (A) is applied to the enteric coating surrounding the core tablet.

2. The controlled release methylphenidate tablet as defined in claim 1 wherein:
(A) the immediate release methylphenidate coating consists of;
  (a) 40-50 weight percent based upon the total weight of the immediate release coating of methylphenidate or a pharmaceutically acceptable salt or isomer thereof;
  (b) 45-60 weight percent based upon the total weight of the immediate release coating of a binder; and
  (c) 0.01-2 weight percent based upon the total weight of the immediate release coating of a stabilizer;
(B) the controlled release methylphenidate core tablet consists of:
  (a) a compressed mixture consisting of:
    (i) 10-25 weight percent based upon the total weight of the compressed mixture of methylphenidate or a pharmaceutically acceptable salt or isomer thereof;
    (ii) 3-40 weight percent based upon the total weight of the compressed mixture of a hydrogel polymer;
    (iii) 45-85 weight percent based upon the total weight of the compressed mixture of a diluent; and
    (iv) 0.1-10 weight percent based upon the total weight of the compressed mixture of a lubricant; and
  (b) an enteric coating surrounding the core tablet consisting of;
    (i) 45-80 weight percent based upon the total weight of the enteric coating of the combination of enteric polymers;
    (ii) 1-5 weight percent based upon the total weight of the enteric coating of a plasticizer;
    (iii) an anti-sticking agent; and
    (iv) optionally a surfactant.

3. The controlled release tablet of claim 1 wherein the at least one additional enteric polymer is a methacrylic acid copolymer.

4. The controlled release methylphenidate tablet as defined in claim 3 wherein the $T_{max2}$ occurs about 7 to 9 hours and declines to about 1.4 ng/ml in about 14 to 18 hours.

5. The controlled release methylphenidate tablet of claim 2 wherein the compressed mixture of the core tablet consists of 0.5-5 weight percent based upon the total weight of the compressed mixture of a lubricant.

* * * * *